United States Patent [19]

Wilhelm

[11] Patent Number: 5,238,488
[45] Date of Patent: Aug. 24, 1993

[54] PROCESS AND SOLUTION FOR TRANSFORMING INSOLUBLE MERCURY METAL INTO A SOLUBLE COMPOUND

[75] Inventor: Stanley M. Wilhelm, Tomball, Tex.

[73] Assignee: Gas Research Institute, Chicago, Ill.

[21] Appl. No.: 858,126

[22] Filed: Mar. 26, 1992

[51] Int. Cl.$^5$ ............................................. C01G 17/00
[52] U.S. Cl. ......................................................... 75/742
[58] Field of Search ................................... 75/742, 711

[56] References Cited

U.S. PATENT DOCUMENTS

| | | | |
|---|---|---|---|
| 3,437,476 | 4/1969 | Dotson | 75/742 |
| 4,094,777 | 6/1978 | Sugier et al. | 210/32 |
| 4,474,896 | 10/1984 | Chao | 502/216 |
| 4,693,731 | 9/1987 | Tarakad et al. | 55/72 |
| 4,764,219 | 8/1988 | Yan | 134/2 |
| 4,786,483 | 11/1988 | Audeh | 423/210 |
| 4,830,829 | 5/1989 | Craig, Jr. | 422/7 |
| 4,915,818 | 4/1990 | Yan | 208/251 |
| 5,013,358 | 5/1991 | Ball | 75/742 |

FOREIGN PATENT DOCUMENTS 319615 6/1989 European Pat. Off. .

OTHER PUBLICATIONS

Talasek, R. T. and Syllaois, A. J., "Reaction Kinetics of $Hg_{1-x}Cd_xTe/Br_2-CH_3OH$," J. Electrochem. Soc., vol. 132, No. 3, pp. 656–659 (1985).

Cotton, F. A. and Wilkinson, G., Advanced Inorganic Chemistry; John Wiley and Sons, pp. 610–613 (1988).

Bond, A. M., J. Amer. Chem. Soc., vol. 109, No. 7, pp. 1969–1980 (1987) "Voltammetric, Coulometric, Mercury-199 . . . ".

Boudon, C. Peter, F. and Gross, M., "Anodic Oxidation of the Mercury Electrode in the Presence of Macrobicyclic Ligands," J. Electroanal. Chem. vol. 135, pp. 93–102 (1982).

Primary Examiner—Peter D. Rosenberg
Attorney, Agent, or Firm—Speckman, Pauley & Fejer

[57] ABSTRACT

A process and solution for transforming insoluble mercury metal into a soluble compound. The process includes oxidizing elemental mercury to form mercury cations, contacting the mercury cations with a complexing agent to form a soluble complex, and dissolving the soluble complex with a solvent. The solution contains an oxidizing agent, a complexing agent and a solvent.

12 Claims, 4 Drawing Sheets

PROCESS AND SOLUTION FOR TRANSFORMING INSOLUBLE MERCURY METAL INTO A SOLUBLE COMPOUND

BACKGROUND OF THE INVENTION

Mercury contaminates aluminum cold box equipment by its precipitation from gaseous and liquid streams during liquefaction and separation processes. Its precise form upon precipitation is not known conclusively; however, it is hypothesized that it forms finely dispersed aggregates that deposit on the walls of aluminum piping. Upon warming of the cold box during shut down, a portion of the mercury coalesces and can form droplets and in extreme cases, pools.

The presence of mercury in natural gas and hydrocarbon streams and the resultant liquid metal embrittlement problems encountered in low temperature processing equipment stimulated various approaches to removing the mercury both from the process streams and the equipment. A recent patent[1] described the use of alkali polysulfides to remove trace amounts of mercury from liquid hydrocarbons at a pH range of 8–11. Another patent[2] used an ionexchange resin containing active thiol groups that removed more than 97 percent of the mercury from hydrocarbons. A method for treating mercury contaminated aluminum surfaces rendered the mercury and amalgam harmless with the use of hydrogen sulfide in a solvent.[3]

1. Yan Tsoung Y., U.S. Pat. No. 4,915,818; Mobil Oil Corporation (1990).
2. Duisters. Henricus Antonius Maria and Van Geem, Paul Christiaan, Eur. Patent Appl. EP 319,615; Stamicarbon BV (1989).
3. Craig, Howard L., U.S. Pat. No. 4,830,829; Mobil Oil Corporation (1987).

A process removed hydrogen sulfide and mercury from natural gas using an alkali metal peroxomonosulfate salt.[4] A clean up procedure decontaminated equipment containing mercury by circulating a solvent containing sulfur, $H_2S$, sulfides or alkylthiol through the equipment to produce mercury sulfide.[5] Mercury was removed from natural gas by utilizing an absorbing hydrocarbon which was subsequently separated out.[6] Zeolite or alumina was treated with sulfur or sulfur compounds which removed mercury from natural gas or liquid hydrocarbon streams.[7] Similarly, mercury was removed from a gas or liquid by passing it over alumina or silica containing a copper sulfide.[8]

4. Audeh, Costandi A., U.S. Pat. No. 4,786,483; Mobil Oil Corporation (1988).
5. Yan, Tsoung Y., U.S. Pat. No. 4,764,219; Mobil Oil Corporation (1988).
6. Taraked, Ramanathan R., Crawford, Duffer B., U.S. Pat. No. 4,693,731; MW Kellogg Company (1987).
7. Chao, Chien C., U.S. Pat. No. 4,474,896; Union Carbide Corporation (1983).
8. Sugier, Andre and laVilla, Florentino, U.S. Pat. No. 4,094,777; Institut Francais du Petrole (1978).

SUMMARY OF THE INVENTION

The technical problem addressed in this invention involves removing mercury from cold box equipment during shut down periods. This conceivably could be when the equipment is cryogenic (←−100 F.) or under ambient conditions. Several removal scenarios were examined for feasibility:

1. Physical removal using an abrasive ($Al_2O_3$) slurry was assessed as unfeasible because of the inability to control hydrodynamics in the complex geometry of the cold box. It is likely that mercury collects in dead spots that may not be completely accessible.

2. Amalgamation was assessed in the context of introducing metals that would form solid amalgams (similar to dental amalgams). It was thought that the completeness of such reactions could not be adequately controlled.

3. Aqueous oxidation of mercury was scrutinized, however, water is somewhat detrimental to the equipment. Acidic water is corrosive to the aluminum and the kinetics of oxidation are generally slow in water. Peroxides, bromine, nitric acid and hypochlorite oxidizing agents were examined conceptually for feasibility.

The removal scenario finally decided upon was to use an oxidizing agent in conjunction with both a non-aqueous solvent and a sequestering agent. The sequestering agent is a compound which forms a soluble (in the solvent) complex with oxidized mercury ($Hg^+$, $Hg^{2+}$). As will be discussed, this hypothesis proved to be fortuitous in providing excellent kinetics of mercury removal. The system so described would function by being pumped through a contaminated cold box. The mercury in place would oxidize, complex to a soluble species and thereby be removed from the equipment, presumably to an exchange resin bed (to remove the complex) or to a thermal cycle (to precipitate the complex) or to a chemical neutralization step (to reduce the complex back to elemental mercury).

The technical tasks necessary to arrive at a formulation to achieve mercury removal included selection of a solvent system, a sequestering agent and an oxidizing agent. Numerous combinations were scrutinized from the stand point of thermodynamics (stability) and kinetics (rate of reaction).

DESCRIPTION OF PREFERRED EMBODIMENTS

Figure 1:
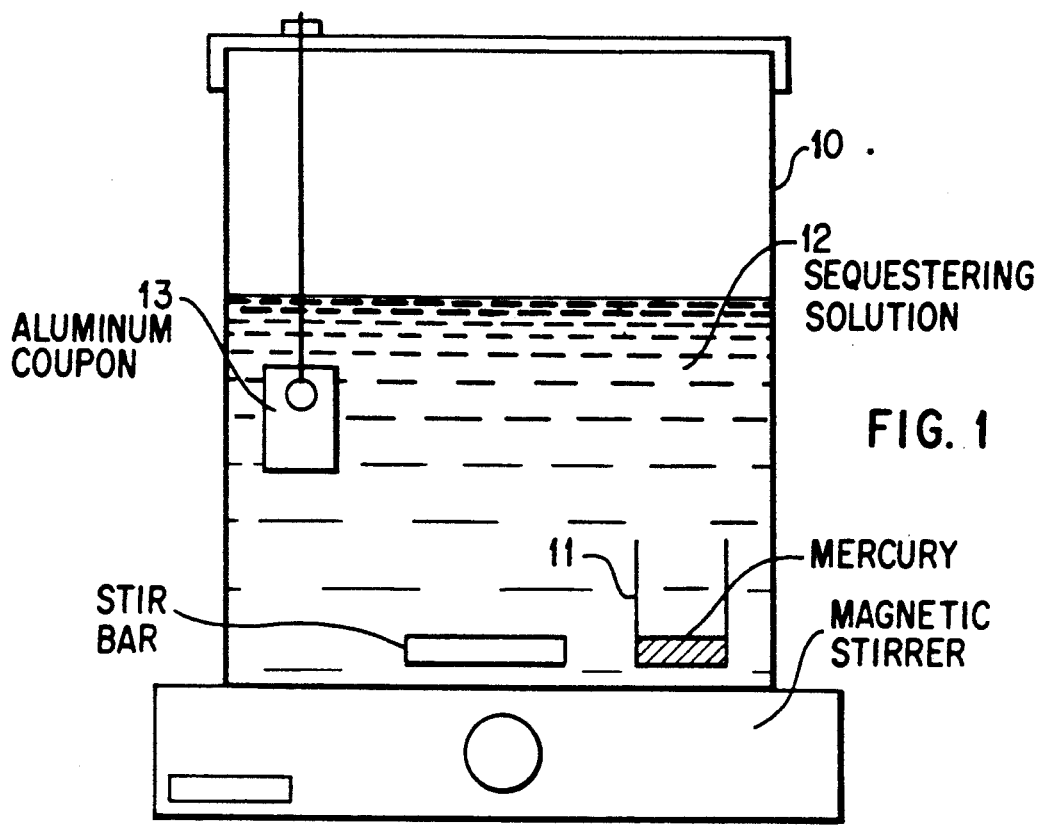
FIG. 1 is a diagrammatic view of an apparatus for mercury oxidation sequestering studies for low surface area/low flow rate.

Known methods for removal of mercury before it reaches the cold box are effective; however, that does not address the problem where contamination already exists. The efforts to decontaminate existing systems rely on the formation of mercury sulfides which are insoluble and difficult to remove from inaccessible recesses. In addition, they require alkaline conditions which can damage the protective oxide on the aluminum.

Mercury, although it is a heavy metal, is remarkably volatile. Its vapor pressure at 77 F. is $1.3 \times 10^{-3}$ mm which explains its presence in natural gas streams. It also presents a health hazard to workers exposed to it because of its high toxicity.

Mercury combines directly with halogens and other non-metals such as sulfur, selenium and lead.

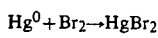
$$Hg^0 + Br_2 \rightarrow HgBr_2$$

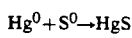
$$Hg^0 + S^0 \rightarrow HgS$$

The reaction rate of bromine with mercury in methanol was found to be proportional to the bromine concentration.[9] $HgBr_2$ is quite soluble in methanol. Bromine, though, is known to also attack aluminum. HgS is very insoluble in MeOH and water having a solubility product of $10^{-54}$. While the presence of water causes some hydrolysis of the $Hg^{2+}$ and $S^{2-}$, the solubility remains low.[10]

9. Talasek, R. T. and Syllaois, A. J., J. Electrochem. Soc., (1983), 132, p656.
10. Cotton and Wilkinson, Advanced Inorganic Chemistry; John Wiley and Sons, (1988), p611. The most common oxidation of mercury is to the dication:

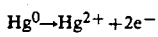
$$Hg^0 \rightarrow Hg^{2+} + 2e^-$$

Instead of the monocation the dimer is preferentially formed:

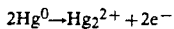
$$2Hg^0 \rightarrow Hg_2^{2+} + 2e^-$$

which rapid and reversibly undergoes disproportionation:

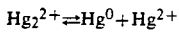
$$Hg_2^{2+} \rightleftharpoons Hg^0 + Hg^{2+}$$

Mercury also combines with other metals like zinc or silver to form amalgams; but, these will still attack aluminum while in the liquid form. In the absence of physical mixing, it is sometimes difficult to get the desired stoichiometry for a solid product.

Electroless plating offers greater mobility to the amalgamating metal. Strongly alkaline conditions are often required for the plating solutions, however, which is incompatible with an aluminum system.

Mercury forms coordination complexes with oxygen, sulfur, phosphorous and nitrogen containing compounds. The most common are the sulfur complexes with thiols (R-S-H compounds) and dithiocarbamic acids[11] ($R_2NCSSH$). The most common[12] is a complex with diethyldithiocarbamic acid:

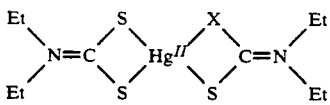

and a more complicated species $[Hg_5(Et_2NCSS)_8]^{2+}$
11. Cotton and Wilkinson, Advanced Inorganic Chemistry; John Wiley and Sons, (1988), p613.
12. Bond, A. M., J. Amer. Chem. Soc., (1987), 109 p1969.

Other compounds known to complex mercury are thiocarbamic acids ($R_2CSSH$), thiocarbazones (RNNSCNHNHR) and cryptates.[13]

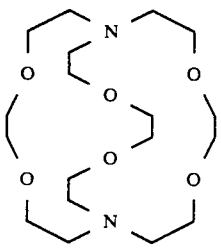

Hexaoxa-1,10-diazabicylohexacosane
(cryptate 2,2,2)

Cryptates are strong complexers of mercury ions. The mercury ion becomes entrapped within the cage like structure and coordinated to the nitrogen atoms.
13. Boudon, Corinne, Peter, Francois and Gross, Maurice, J. Electroanal. Chem., (1982), 135 p93-102.

A practical approach to removal of mercury from complex aluminum equipment would ideally meet the following criteria:

1. Utilize an industrially available solvent that is relatively inexpensive.
2. Utilize a solvent that would be easy to remove upon completion.
3. Utilize a solvent with a freezing point below −40° F.
4. All components would remain in solution to temperatures of −40° F.
5. Contain an oxidizing agent that would aid the dissolution of mercury and oxidize exposed 5083 aluminum metal to the inert oxide while not attacking the metal oxide itself.
6. Contain a sequestering agent that would complex mercury into a soluble form but not attack aluminum or its protective oxide.

Solvents were selected to meet the criteria of freezing point, cost and ease of removal from the system. The solvents were then tested for their ability to dissolve a typical sequestering agent.

Nitric acid, a known oxidizer for mercury, was tested at various concentrations in the solvent to determine its compatibility with the 5083 aluminum. The rate of aluminum dissolution was then determined as a function of nitric acid concentration and solvent composition. Sequestering agents were then screened to determine optimum mercury dissolution ability.

Figure 2:
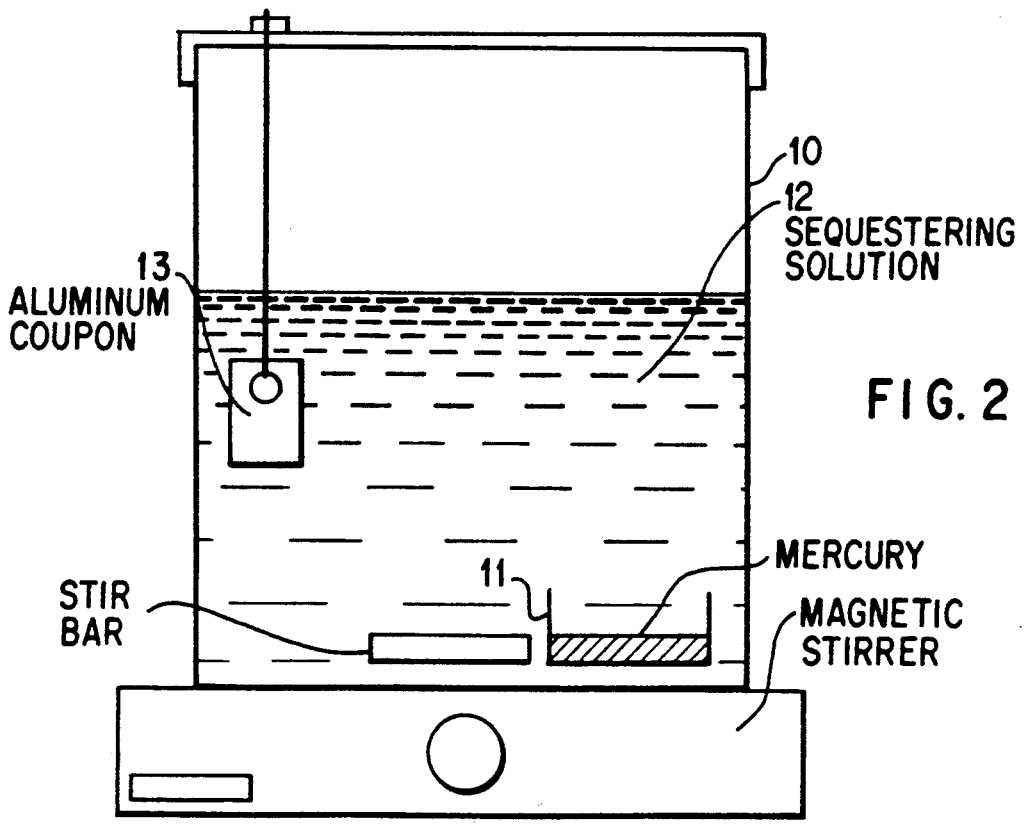
FIG. 2 is a diagrammatic view of an apparatus for mercury oxidation sequestering studies for moderate surface area/moderate flow rate.

The solvent system, nitric acid and sequestering agent were then examined under the following situations:

1. Simulation of mercury in a recessed crack or joint (i.e. low surface and limited flow of sequestering mixture) (see FIG. 1).
2. Mercury on a flat surface (i.e. greater surface area and unhindered flow of sequestering solution) (see FIG. 2).
3. Saturation level of mercury in the sequestering solution (i.e. elevated temperature and stirred mercury) (see FIG. 3).

EXAMPLE I

The sequestering agents were reagent grade, solvents were practical grade and the water was distilled. Nitric acid was 15.9N reagent grade. Fresh instrument grade mercury was used in each experiment.

Aluminum coupons were 5083 Al, 1-inch×2-inch×1/16-inch. Mercury analyses were performed by ACS Labs (16203 Park Row #100, Houston, Tex. 77084) and utilized direct current argon plasma emission.

The solubility of the sodium salt of diethyldithiocarbamic acid (DEDCA) was determined in various solvent systems at room temperature and −40 F. One gram of acid was mixed with 50 ml of solvent and the solubility of the dithiocarbamate noted after two hours. The test was repeated using two grams per 50 ml of solvent. The results are displayed in Table 1. The mercury dissolution rates for low flow/low surface area and the aluminum dissolution rates were determined at room temperature in various solvent compositions with and without a sequestering agent.

Two liter portions of a methanol/water solvent mixture (from 100 percent water to 90:10 methanol:water) were utilized in each experiment. The nitric acid was first added to the water which was subsequently added to the methanol in a 4 liter beaker 10. The sequestering agent was then added. Mercury (20 g/l) in a 50 ml beaker 11 was positioned at the bottom of the solution 12 (see FIG. 1). A pre-weighed Al 5083 coupon 13 was suspended in the solution. The mixture was stirred and aliquots taken at 0.25, 1, 5 and 24 hours for mercury analysis. The Al coupon 13 was rinsed with distilled water and acetone, dried and weighed. The results are tabulated in Tables 2 and 3.

EXAMPLE II

Figure 3:
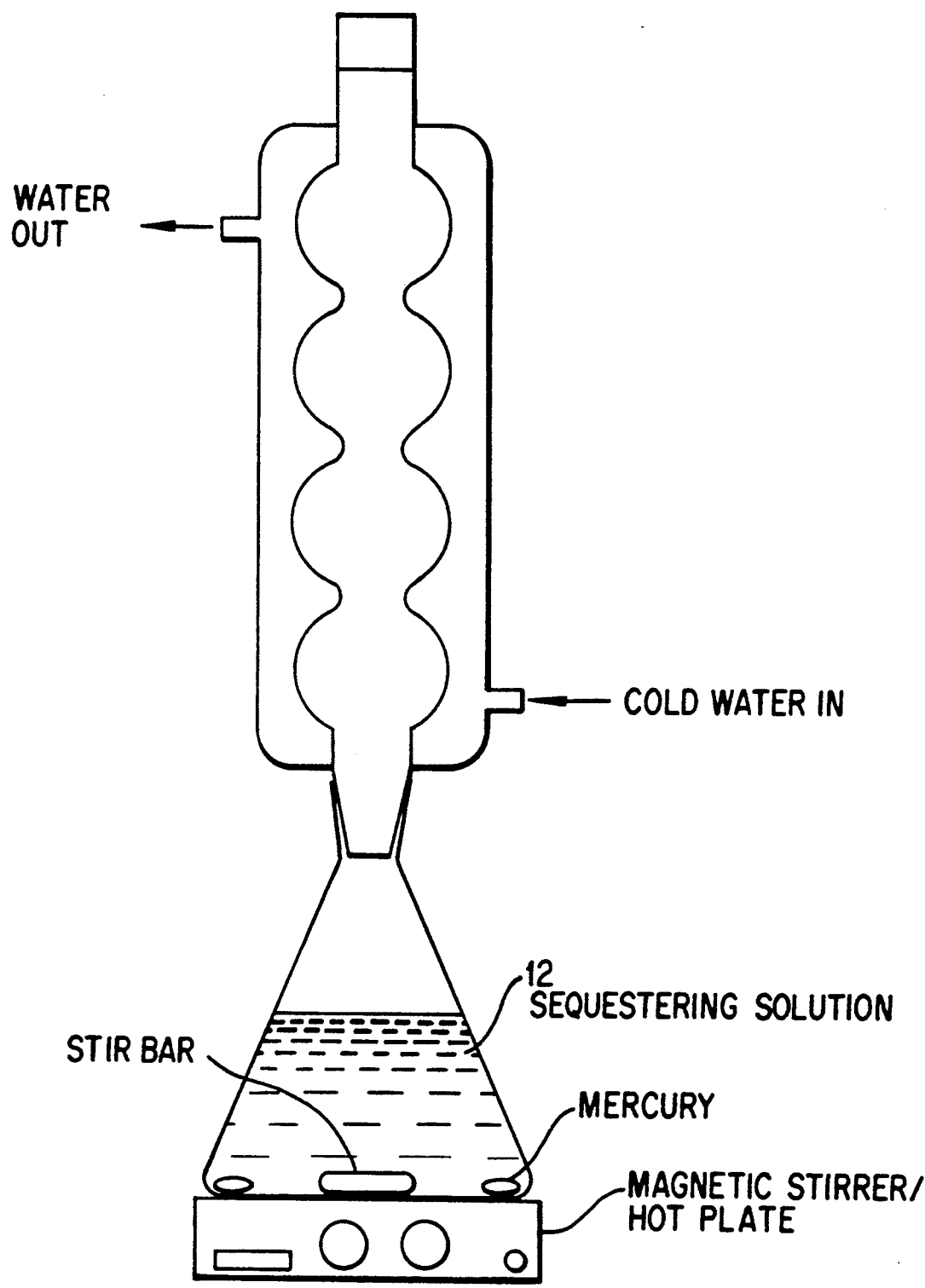
FIG. 3 is a diagrammatic view of an apparatus for mercury saturation of sequestering solution for high surface area/high flow rate.

A similar experiment was conducted in 95:5 methanol/water the results of which are displayed in Table 4. The mercury dissolution rates for moderate flow/moderate surface area were run similarly as in FIG. 2. In addition, other sequestering agents, dibutyldithiocarbamic acid zinc salt (DBDCA), diphenylthiocarbazone (DPTC), ethylenediaminetetraacetic acid (EDTA), hexaoxa -1,10-diazabicyclohexacosane (cryptate 2,2,2) and a mixture of DEDCA and DBDCA were screened in like manner to determine their mercury dissolution effectiveness. DEDCA, EDTA and DPTC were not completely soluble at 0.1M. They were run as saturated solutions in equilibrium with the solid. Table 5 summarizes the results. The saturation level of mercury in 90:10 methanol:water/0.5M DEDCA/0.1N nitric acid was determined by heating the sequestering solution 12 to reflux with rapid stirring as shown in FIG. 3. This result is also included in Table 5. Upon cooling crystals precipitated.

EXAMPLE III

Bromine was examined as an alternate oxidant. In a 4 liter beaker an aluminum 5083 coupon was suspended in a solution of 2 liters of methanol and 32 g of bromine. After 48 hours, the aluminum coupon had completely dissolved. With 3.2 g bromine, the aluminum had a 12 percent weight loss after 48 hours.

Elemental sulfur is known to combine with mercury to form mercury sulfides. Likewise organic sulfur compounds are known to form sulfides or complexes with mercury. This invention focuses on the active thiol compounds of thiocarbamic acids, thiocarbazones and cryptates as complex formers for mercury.

The thiocarbamic acids, however, have the advantage of ease of preparation, low cost and high solubility in organic solvents. Therefore the initial thrust of this project was to determine the feasibility of using diethyldithiocarbamic acid sodium salt DEDCA in low freezing point solvents. Table 1 shows the results of solubility studies of DEDCA in various alcohols, glycols and water. Methanol proved to be not only the best solvent for DEDCA but has other significant advantages in that it is relatively inexpensive and readily available. In addition, it is the lowest boiling of any of the solvents considered which will facilitate its removal from field aluminum heat exchangers.

Figure 4:
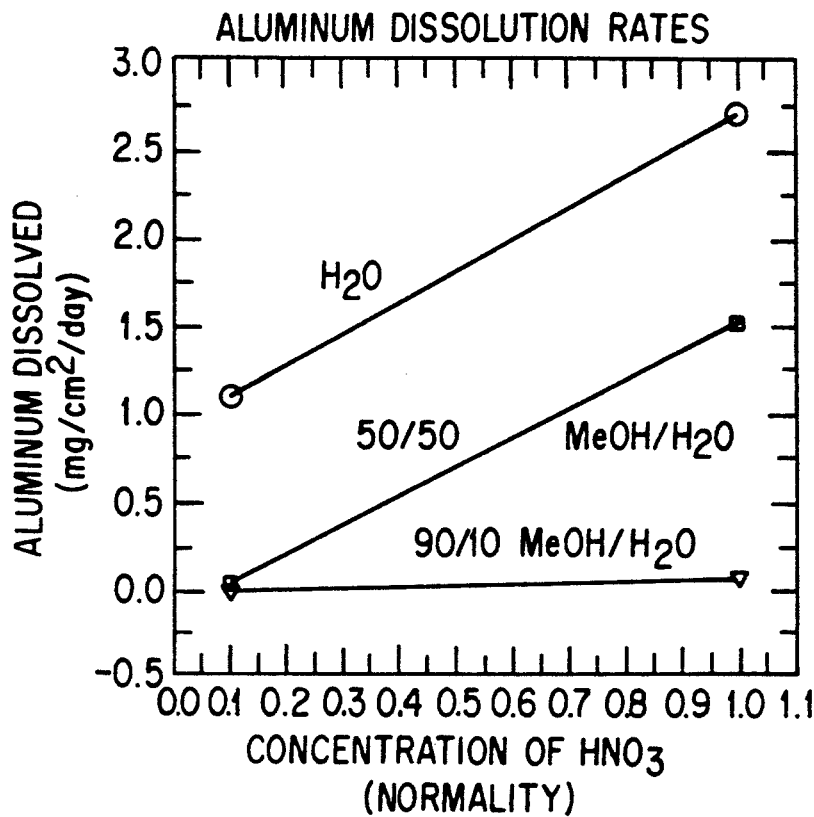
FIG. 4 is a graph showing the effect of solvent on aluminum dissolution rate for 0.1M DEDCA solutions.

The most common oxidants for mercury are nitric acid and bromine. However, any oxidizing agent strong enough to attack mercury must, for this application, leave the aluminum-aluminum oxide surface intact. High concentrations of nitric acid are usually required to oxidize mercury. Therefore, the effect of nitric acid concentration was measured for both mercury dissolution rate as well as aluminum dissolution rate. Table 2 shows the minimum of the etch rate of aluminum dissolution and the maximum mercury dissolution is with 0.1N nitric acid in 90:10 methanol:water. This is fortuitous in that at this concentration, the nitric acid is a strong enough oxidizer to reform the oxide coating where aluminum metal is exposed, yet not acidic enough to cause any significant loss of aluminum (see FIG. 4).

The use of bromine as an oxidizer for mercury in an aluminum system was ruled out due to the excessively high aluminum dissolution rate even with 0.01M bromine in methanol.

Table 3 shows the effect of the sequestering agent DEDCA concentration on mercury dissolution rate at several concentrations of oxidizing acid under conditions of low mercury surface area and low sequestering solution flow over the mercury surface. The optimum concentration was 0.5M DEDCA. Additional attempts to increase the rate showed no further improvement and are summarized in Table 4.

Figure 5:
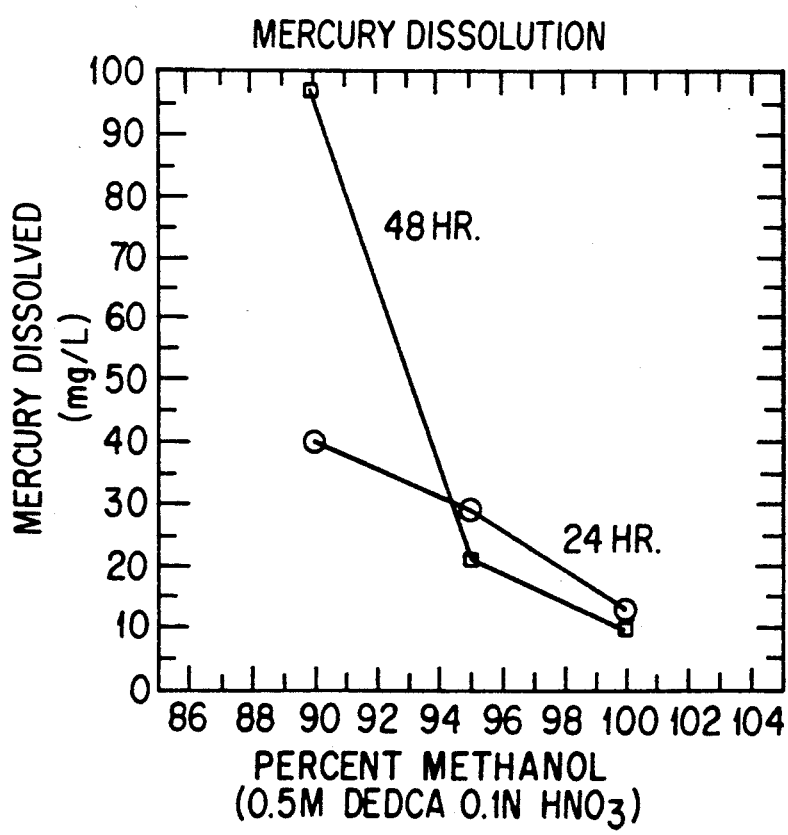
FIG. 5 is a graph showing the effect of methanol water ratio on mercury dissolution rate.
Figure 6:
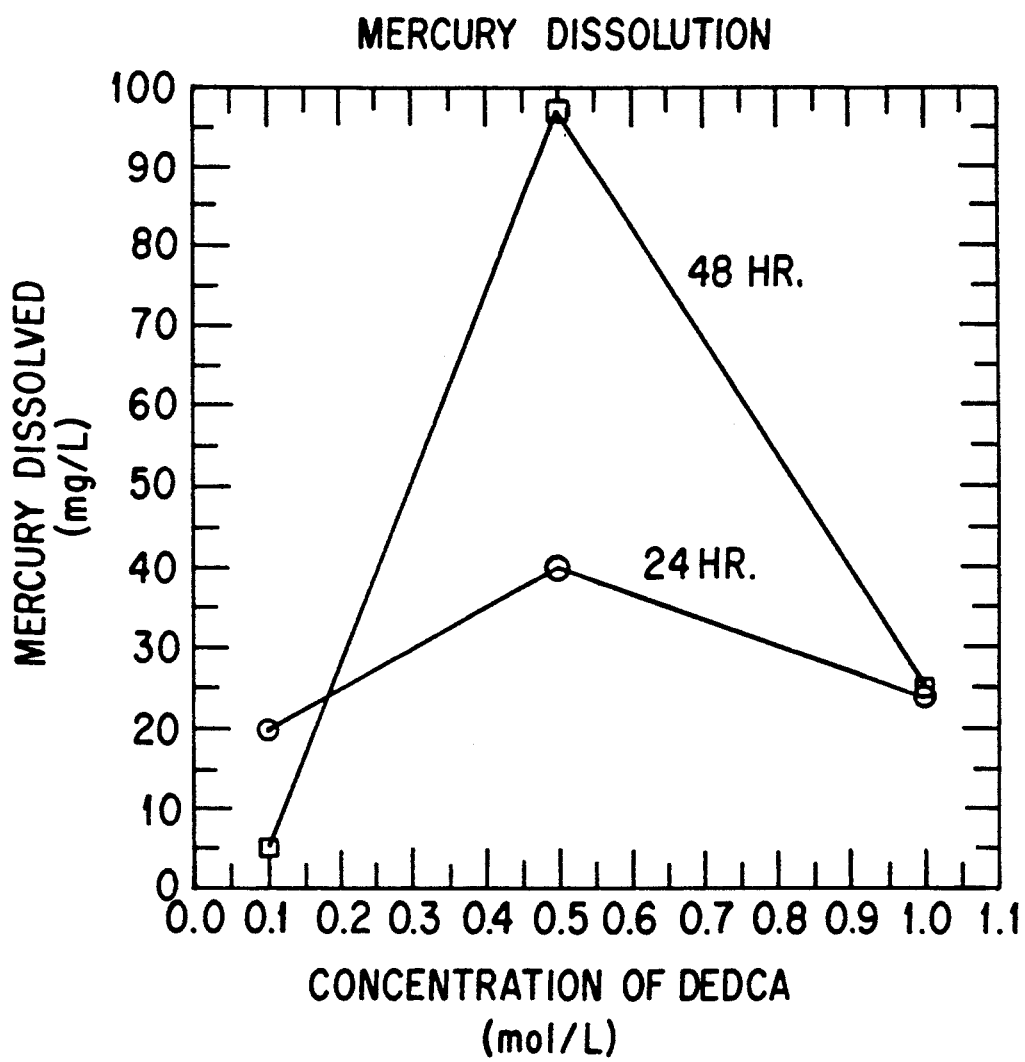
FIG. 6 is a graph showing the effect of DEDCA concentration mercury dissolution rate.

The results for the 90:10 methanol:water/0.1N nitric acid without DEDCA were parallel for both low surface/low flow and moderate surface/moderate flow. Without the DEDCA there is little dissolution or oxidation of mercury regardless of the mercury/solution contact ratio. Other sequestering agents failed to improve upon the results of DEDCA. The solubility of DPTC and EDTA was not high enough to form 0.1M solutions. These were run in equilibrium with the solid. The results are summarized in Table 5. The cryptate was soluble but failed to facilitate the oxidation enough to complex the mercury.[14] DBDCA appeared to lower the surface tension of the mercury, as pools of mercury spread out in its presence. However, it was less effective than DEDCA in sequestering the mercury. It also failed to completely dissolve in the solvent mixture. Likewise a mixture of DEDCA and DBDCA did not improve over the DEDCA alone. With 0.1M solutions of DEDCA, saturation appeared to be reached before 24 hours, but with 0.5M DEDCA not only was the total mercury dissolved higher after 24 hours, but it more than doubled after an additional 24 hours (see FIG. 6). This was not the case, however, upon changing the solvent ratio to 95:5 methanol:water or to 100 percent methanol (see FIG. 5). As with the low surface/low flow, they saturated before 24 hours (see Table 4).

14. Boudon, Corinne, Peter, Francois and Gross, Maurice, J. Electroanal. Chem., (1982), 135 p93–102.

It is interesting to note that the 90:10 methanol:water/0.5M DEDCA without nitric acid was able to sequester 15 mg/l of mercury. This indicates that the DEDCA itself is an effective oxidizer for mercury (see Appendix A) the presence of nitric acid, however, enhances the rate.

At high surface/high flow and elevated temperature (140 F.) the total dissolved mercury reached 220 mg/l after 24 hours and 330 mg/l after 48 hours. There was no aluminum dissolution after even after 3 days at reflux. Upon cooling the hot solution, crystals appeared indicating formation of a DEDCA complex. If this proves to be the case, the mercury can be continuously removed by cycling the Hg-saturated solution through a cooling and filtering apparatus.

It appears that the 90:10 methanol water/0.5M DEDCA/0.1N $HNO_3$ sequestering solution has the capacity to be practical and effective in removing mercury from complex refinery equipment. This method leaves no insoluble by-products and is easily rinsed from the system with methanol.

Since the sequestering solution is soluble to $-40$ F. and is oxidizing it is also possible that it could diffuse under cold solid mercury to heal any discontinuities of the oxide surface of the aluminum to prevent amalgation upon warming the system to temperatures that would increase the rate of mercury dissolution to practical levels.

TABLE 1

| Solubility of Diethyldithiocarbamic Acid (DEDCA) Sodium Salt | | | | | |
|---|---|---|---|---|---|
| Solvent/ CoSolvent | Freezing Point (F) | DEDCA 20 g/l | | DEDCA 40 g/l | |
| | | 75 F | −109.3 F | 75 F | 109.3 F |
| $H_2O$ | 32 | >20* | Frozen | >40 | Frozen |
| Ethanol | −178 | >20 | >20 | >20 | <40  <40 |
| Methanol | −137 | >20 | >20 | >40 | >40 |
| Isopropanol | −298 | >20 | >20 | >20 | <40  <40 |
| Ethylene Glycol | 11 | >20 | Frozen | >40 | Frozen |
| 1,2 Propanediol | — | >20 | Frozen | >20 | <40 Frozen |
| 50% $H_2O$, 50% Ethylene Glycol | — | >20 | Frozen | >20 | <40 Frozen |
| 50% $H_2O$, 50% Ethylene Glycol + 2% 1 n-Butanol | — | >20 | Frozen | >20 | <40 Frozen |
| $H_2O$, 50% 1,2 Propanediol | — | >20 | Frozen | >40 Frozen | |
| 50% $H_2O$, 50% Propanediol + 2% 1 n-Butanol | — | >20 | Frozen | >20 | <40 Frozen |
| $H_2$ + 2% 1, n-Butanol | — | >20 | Frozen | >20 | <40 Frozen |

*Based on 20 g acid/liter solution

TABLE 2

| | | | Mercury Oxidation Test Matrix | | | |
|---|---|---|---|---|---|---|
| Solvent | Complexing Agent Concentration mol/l | Nitric Acid mol/l | Mercury area/vol $cm^2$/l | Sample Time (hr) | Mercury Dissolution Rate (g/$cm^2$/hr) | Total Weight of Hg (g/l) | Aluminum Dissolution Rate (g/$cm^2$/day) |
| $H_2O$ | | 0.1 | 3.61 | 0.25 | 1.33 E-5 | | |
| | | | | 1 | 2.75 E-7 | | |
| | | | | 5 | 5.44 E-8 | | |
| | | | | 24 | 1.81 E-7 | 1.6 E-5 | 1.1 E-3 |
| $H_2O$ | | 1.0 | 3.61 | 0.25 | 1.11 E-6 | | |
| | | | | 1 | 2.75 E-7 | | |
| | | | | 5 | 8.44 E-7 | | |
| | | | | 24 | 8.12 E-5 | 1.57 E-3 | 2.7 E-3 |
| MeOH:$H_2O$ 50:50 | | 0.1 | 3.61 | 0.25 | 5.75 E-3 | | |
| | | | | 1 | 1.77 E-4 | | |
| | | | | 5 | 8.44 E-6 | | |
| | | | | 24 | 8.12 E-8 | 8.0 E-6 | 3.9 E-5 |
| MeOH:$H_2O$ 50:50 | | 1.0 | 3.61 | 0.25 | 1.35 E-4 | | |
| | | | | 1 | 8.02 E-4 | | |
| | | | | 5 | 3.12 E-5 | | |
| | | | | 24 | 3.30 E-5 | 2.98 E-3 | 1.5 E-3 |
| MeOH:$H_2O$ 90:10 | | 0.1 | 3.61 | 0.25 | 4.51 E-3 | | |
| | | | | 1 | 9.70 E-5 | | |
| | | | | 5 | 3.76 E-4 | | |
| | | | | 24 | 4.83 E-5 | 5.24 E-3 | 3.8 E-6 |
| MeOH:$H_2O$ 90:10 | | 1.0 | 3.61 | | 3.64 E-3 | | |
| | | | | | 8.87 E-4 | | |
| | | | | | 1.94 E-4 | | |
| | | | | | 3.53 E-5 | 3.48 E-3 | 5.4 E-5 |

TABLE 3

| | | | Mercury Oxidation Test Matrix | | | |
|---|---|---|---|---|---|---|
| Solvent | Complexing Agent Concentration mol/l | Nitric Acid mol/l | Mercury area/vol $cm^2$/l | Sample Time (hr) | Mercury Dissolution Rate (g/$cm^2$/hr) | Total Weight of Hg (g/l) | Aluminum Dissolution Rate (g/$cm^2$/day) |
| MEOH:$H_2O$ 90:10 | 0.1 DEDCA | 0.1 | 3.61 | 0.25 | 2.79 E-4 | | |
| | | | | 1 | 1.61 E-4 | | |
| | | | | 5 | 1.41 E-4 | | |
| | | | | 24 | 5.86 E-5 | 6.2 E-3 | 0.0 |
| MEOH:$H_2O$ 90:10 | 0.5 DEDCA | 0.1 | 3.61 | 0.25 | 6.39 E-4 | | |
| | | | | 1 | 5.36 E-4 | | |
| | | | | 5 | 5.21 E-4 | | |
| | | | | 24 | 3.05 E-4 | 2.9 E-2 | 0.0 |
| MEOH:$H_2O$ 90:10 | 0.1 DEDCA | 1.0 | 3.61 | 0.25 | 1.02 E-5 | | |
| | | | | 1 | 2.52 E-6 | | |
| | | | | 5 | 5.00 E-7 | | |
| | | | | 24 | 1.04 E-7 | 1.0 E-5 | 3.5 E-5 |
| MEOH:$H_2O$ | 0.5 | 1.0 | 3.61 | 0.25 | 1.34 E-3 | | |

TABLE 3-continued

Mercury Oxidation Test Matrix

| Solvent | Complexing Agent Concentration mol/l | Nitric Acid mol/l | Mercury area/vol cm²/l | Sample Time (hr) | Mercury Dissolution Rate (g/cm²/hr) | Total Weight of Hg (g/l) | Aluminum Dissolution Rate (g/cm²/day) |
|---|---|---|---|---|---|---|---|
| 90:10 | DEDCA | | | 1 | 3.21 E-5 | | |
| | | | | 5 | 6.60 E-5 | | |
| | | | | 24 | 3.20 E-5 | 2.8 E-3 | 1.2 E-5 |

TABLE 4

Mercury Oxidation Test Matrix

| Solvent | Complexing Agent Concentration mol/l | Nitric Acid mol/l | Mercury area/vol cm²/l | Sample Time (hr) | Mercury Dissolution Rate (g/cm²/hr) | Total Weight of Hg (g/l) | Aluminum Dissolution Rate (g/cm²/day) |
|---|---|---|---|---|---|---|---|
| MEOH:H₂O 95:05 | 1.0 DEDCA | 0.05 | 3.61 | 24 | 1.92 E-5 | 1.6 E-3 | |
| | | | | 48 | 1.07 E-5 | 1.8 E-3 | 4.26 E-5 |
| MEOH:H₂O 95:05 | 0.25 DEDCA | 0.05 | 3.61 | 24 | 4.71 E-6 | 5.0 E-4 | |
| | | | | 48 | 2.79 E-6 | 6.0 E-4 | 7.75 E-5 |
| MEOH:H₂O 95:05 | 1.0 DEDCA | 0.2 | 3.61 | 24 | 2.17 E-4 | 1.8 E-2 | |
| | | | | 48 | 1.13 E-4 | 1.9 E-2 | 5.42 E-5 |
| MEOH:H₂O 95:05 | 0.25 DEDCA | 0.2 | 3.61 | 24 | 2.66 E-4 | 2.8 E-4 | |
| | | | | 48 | 9.37 E-7 | 2.0 E-4 | 3.80 E-6 |

TABLE 5

Mercury Oxidation Test Matrix

| Solvent | Complexing Agent Concentration mol/l | Nitric Acid mol/l | Mercury area/vol cm²/l | Sample Time (hr) | Mercury Dissolution Rate (g/cm²/hr) | Total Weight of Hg (g/l) | Aluminum Dissolution Rate (g/cm²/day) |
|---|---|---|---|---|---|---|---|
| MEOH:H₂O 90:10 | 0 | 0.1 | 6.62 | 24 | 1.0 E-5 | 1.6 E-3 | |
| | | | | 48 | 2.6 E-6 | 8.2 E-4 | 2.0 E-5 |
| MEOH:H₂O 90:10 | <0.1* DPTC | 0.1 | 6.62 | 24 | 4.2 E-5 | 6.7 E-3 | |
| | | | | 48 | 4.1 E-6 | 1.3 E-3 | 1.9 E-5 |
| MEOH:H₂O 90:10 | <0.1* EDTA | 0.1 | 6.62 | 24 | 4.4 E-6 | 7.0 E-4 | |
| | | | | 48 | 3.2 E-2 | 1.0 E-3 | 3.4 E-6 |
| MEOH:H₂O 90:10 | 0.0027 KRYPTOFIX | 0.1 | 6.62 | 24 | 8.2 E-6 | 1.3 E-3 | |
| | | | | 48 | 2.8 E-6 | 9.0 E-4 | 2.5 E-5 |
| MEOH:H₂O 90:10 | <0.1* DBDCA | 0.1 | 6.62 | 24 | 4.0 E-6 | 6.3 E-4 | |
| | | | | 48 | 4.1 E-6 | 1.3 E-3 | 2.5 E-5 |
| MEOH:H₂O 90:10 | 0.5 DEDCA 0.005 DBDCA | 0.1 | 6.62 | 24 | 1.1 E-4 | 1.8 E-2 | |
| | | | | 48 | 5.0 E-5 | 1.6 E-2 | |
| MEOH:H₂O 90:10 | 0.1 DEDCA | 0.1 | 6.62 | 24 | 1.3 E-4 | 2.0 E-2 | |
| | | | | 48 | 1.6 E-5 | 5.1 E-3 | 3.3 E-5 |
| MEOH:H₂O 90:10 | 0.5 DEDCA | 0.1 | 6.62 | 24 | 2.5 E-4 | 4.0 E-2 | |
| | | | | 48 | 3.1 E-4 | 9.7 E-2 | 1.5 E-5 |
| MEOH:H₂O 90:10 | 1.0 DEDCA | 0.1 | 6.62 | 24 | 1.5 E-4 | 2.4 E-2 | |
| | | | | 48 | 7.9 E-5 | 2.5 E-2 | |
| MEOH:H₂O 95:5 | 0.5 DEDCA | 0.1 | 6.62 | 24 | 1.8 E-4 | 2.9 E-2 | |
| | | | | 48 | 6.6 E-5 | 2.1 E-2 | |
| MEOH:H₂O 90:10 | 0.5 DEDCA | 0 | 6.62 | 24 | 3.6 E-5 | 5.7 E-3 | |
| | | | | 48 | 4.7 E-5 | 1.5 E-2 | |
| MEOH:100% DEDCA | 0.5 | 0.1 | 6.62 | 24 | 8.2 E-5 | 1.3 E-2 | |
| | | | | 48 | 3.2 E-5 | 1.0 E-2 | |
| MEOH:H₂O** 90:10 | 0.5M DBDCA | 0.1 | — | 24 | | 2.2 E-1 | |
| | | | | 48 | | 3.3 E-1 | 0.0 |

*Saturated
**Refluxing MeOH, mercury stirred

CONCLUSIONS

1. DEDCA is the most effective sequestering agent tested in terms of solubility and mercury dissolution ability. The optimum concentration of DEDCA was 0.5M.

2. The methanol:water solvent mixture in a 90:10 ratio provided the best results in terms of high mercury dissolution rates and low aluminum dissolution rates.

3. The nitric acid was most effective at 0.1N. There was some mercury dissolution without the nitric acid, but it was greatly enhanced at 0.1N. At 1.0N nitric acid not only was the mercury dissolution rate low but the aluminum dissolution rate increased to an unacceptable level.

4. The mercury dissolution depends on the exposed surface area of the mercury and the flow rate of sequestering solution over the mercury surface, rather than on the bulk concentration of mercury.

5. The maximum mercury dissolution at room temperature was about 100 mg/l of sequestering solution. However, at 140 F. it approached 500 mg/l.

6. The crystallization of the mercury complex at lower temperatures provides for a process with wherein the sequestered mercury is easily isolated.

7. Bromine as an oxidizing agent for mercury is not feasible in aluminum equipment.

A variety of compounds in solution were screened for their ability to effectively sequester mercury. Diethyldithiocarbamic acid (DEDCA) emerged as the most effective candidate. Optimization of the nitric acid concentration, DEDCA concentration and methanol/water ratio resulted in a solution that has the capability of complexing amounts approaching 0.5 gram of mercury per liter of solution. The rate of dissolution depends on the surface area of mercury exposed to the sequestering solution and the temperature.

I claim:

1. A process for transforming insoluble mercury metal into a soluble mercury compound comprising:
   (a) oxidizing elemental mercury with nitric acid to form mercury cations;
   (b) contacting the mercury cations with an organic compound suitable for forming the soluble mercury compound; and
   (c) dissolving the soluble mercury compound with a solvent.

2. A process according to claim 1 wherein the nitric acid, the organic compound and the solvent are contained in a single solution.

3. A process according to claim 1 wherein the mercury is removed from aluminum.

4. A process according to claim 1 wherein the nitric acid is approximately 0.1N.

5. A process according to claim 1 wherein the organic compound is selected from the group consisting of oxygen containing compounds, sulfur containing compounds, phosphorous containing compounds, nitrogen containing compounds and mixtures thereof.

6. A process according to claim 1 wherein the solvent is a mixture of methanol and water.

7. A process according to claim 1 wherein the solvent has a freezing point below $-40°$ F.

8. A solution for transforming insoluble mercury metal into a soluble mercury compound, the solution comprising: nitric acid, a complexing agent selected from the group consisting of oxygen containing compounds, sulfur containing compounds, phosphorous containing compounds, nitrogen containing compounds and mixtures thereof, and a solvent.

9. A solution according to claim 8 wherein the nitric acid is approximately 0.1N.

10. A solution according to claim 8 wherein the complexing agent is selected from the group consisting of a thiol, a dithiocarbamic acid, a thiocarbamic acid, a thiocarbazone, a cryptate and mixtures thereof.

11. A solution according to claim 8 wherein the solvent is a mixture of methanol and water.

12. A solution according to claim 8 wherein the solvent has a freezing point below $-40°$ F.

* * * * *